United States Patent [19]

Farha, Jr. et al.

[11] 4,026,820
[45] May 31, 1977

[54] SOLID CATALYSTS FOR OXIDATIVE DEHYDROGENATION OF ALKENES OR ALKADIENES TO FURAN COMPOUNDS

[75] Inventors: Floyd E. Farha, Jr.; Marvin M. Johnson; Donald C. Tabler, all of Bartlesville, Okla.

[73] Assignee: Phillips Petroleum Company, Bartlesville, Okla.

[22] Filed: Sept. 29, 1975

[21] Appl. No.: 617,894

Related U.S. Application Data

[62] Division of Ser. No. 389,738, Aug. 16, 1973, Pat. No. 3,928,389.

[52] U.S. Cl. .............................. 252/432; 252/435; 252/437
[51] Int. Cl.² .................... B01J 21/02; B01J 27/14
[58] Field of Search .................. 252/437, 435, 432

[56] References Cited

UNITED STATES PATENTS

| 3,327,008 | 6/1967 | Noddings et al. | 252/437 X |
|---|---|---|---|
| 3,327,009 | 6/1967 | Noddings et al. | 252/437 |
| 3,327,011 | 6/1967 | Noddings et al. | 252/437 |
| 3,398,100 | 8/1968 | Christmann | 252/435 |
| 3,716,545 | 2/1973 | Ripley | 252/437 X |
| 3,784,483 | 1/1974 | Cichowski | 252/437 |
| 3,832,359 | 8/1974 | Freerks et al. | 252/437 X |
| 3,862,910 | 1/1975 | Cichowski | 252/437 X |
| 3,870,764 | 3/1975 | Gichowski et al. | 252/437 X |
| 3,912,763 | 10/1975 | Farha, Jr. et al. | 252/435 X |

*Primary Examiner*—Patrick P. Garvin
*Assistant Examiner*—William G. Wright

[57] ABSTRACT

Alkenes and/or alkadienes are contacted with molecular oxygen and an oxidative dehydrogenation catalyst consisting essentially of phosphorus, iron, and oxygen, with the iron-to-phosphorus atom ratio being in the range of about 2:1 to about 20:1.

17 Claims, No Drawings

SOLID CATALYSTS FOR OXIDATIVE DEHYDROGENATION OF ALKENES OR ALKADIENES TO FURAN COMPOUNDS

This is a divisional of copending application Ser. No. 389,738, filed Aug. 16, 1973, now U.S. Pat. No. 3,928,389.

This invention relates to oxidative dehydrogenation catalysts and the use thereof for the conversion of alkenes and/or alkadienes to furan compounds.

Furan compounds can react readily with oxygen under oxidation conditions to produce ring cleavage and the formation of polymers. Accordingly, the production of furan compounds by the oxidative dehydrogenation of hydrocarbons has generally been avoided. Recently it has been discovered that furan compounds can be produced by the oxidative dehydrogenation of hydrocarbons in the presence of certain specific catalysts without substantial conversion of the furan compounds to undersirable products. The search for additional catalysts suitable for this reaction continues.

Accordingly, it is an object of the present invention to provide a new and improved oxidative dehydrogenation catalyst. Another object of the invention is to provide a new and improved process for the conversion of alkenes or alkadienes to furan compounds. Other objects, aspects and advantages of the invention will be apparent from a study of the specification and the appended claims to the invention.

In accordance with the present invention there is provided an improved catalyst for the production of furan type compounds from alkenes and alkadienes having from 4 to 10 carbon atoms, which catalyst consists essentially of phosphorus, iron, and oxygen wherein the iron-to-phosphorus atom ratio is in the range of about 2:1 to about 20:1, preferably in the range of about 2.5:1 to about 10:1, and more preferably in the range of about 3:1 to about 6:1.

If desired, these catalysts can be supported on conventional solid catalytic support materials, for example zinc oxide, silica, alumina, boria, magnesia, titania, zirconia, and mixtures thereof. Where a catalyst support is employed, the support will generally constitute from about 10 to about 98, preferably from about 75 to about 95, weight percent of the total catalyst composition. Supports having a surface area in the range of about 2 to about 50 $m^2/g$, and preferably in the range of about 5 to about 20 $m^2/g$, are desirable.

The catalysts of the present invention can be prepared by many suitable techniques, for example coprecipitation, impregnation, ion exchange, aqueous or nonaqueous solution or suspension mixing, or dry mixing. In general, any method can be employed which will provide a composition containing the desired elements in the defined proportions, and which has a catalytic surface area in the range of about 0.05 to about 20 $m^2/g$, preferably in the range of about 0.1 to about 5 $m^2/g$. Thus the catalyst components and/or compounds thereof can be combined in any suitable manner. Any compound of iron or phosphorus can be employed in the preparation of the catalyst so long as none of the compounds are detrimental to the final oxidative dehydrogenation catalyst and essentially all of the elements in the compounds employed, other than the iron, phosphorus, and oxygen, are removed from the final catalyst by washing or by volatilazation. However, small or trace amounts of some other elements which can be involved in the preparation of the catalyst can be tolerated in the final catalyst composition. For example, if alkali metal or alkaline earth metal hydroxides are employed in the preparation of the catalyst, very small residual amounts of such alkali metal and alkaline earth metals are not detrimental. Similarly if iron sulfate is employed in the preparation of the catalyst, small residual amounts of sulfur can be tolerated.

Generally, however, the preferred iron compounds are the oxides or phosphates of iron or compounds which are converted to the oxide or phosphate on calcination. Thus, suitable iron compounds include the oxides, phosphates, nitrates, halides, sulfates, oxalates, acetates, carbonates, propionates, tartrates, hydroxides, and the like. Examples of these compounds include iron hydroxide, iron propionate, iron oxide, iron nitrate, iron acetate, iron phosphate, iron chloride, iron carbonate, and the like, and admixtures thereof. The presently preferred phosphorus compounds include the phosphorus oxides, the ammonium phosphates, iron phosphate, and the various forms of phosphoric acid, and the like, and admixtures thereof. Examples of suitable phosphorus compounds are iron phosphate, phosphoric acid, phosphorus pentoxide, diammonium hydrogen phosphate, and the like, and admixtures thereof. The term "phosphate" includes not only the monophosphate ion, $PO_4^{-3}$, but also polyphosphate ions $(PnO_{3n+1})^{-(n+2)}$ and $[PnO_{3n-1}(OH)_2]^{-n}$ in which $n$ is an integer in the range of 2 through 100.

One technique for forming an unsupported catalyst of the present invention comprises mixing one or more phosphorus compounds, and one or more iron compounds.

The compounds can be admixed in the form of dry compounds and then calcined. They can be mixed in the presence of a diluent to form a paste and/or one of the components can be employed in liquid form, such as phosphoric acid, to form the paste. If desired the paste can be dried before calcining. A particle forming step such as pelletizing or screening can precede the drying step or the calcining step.

A technique for forming a supported catalyst of the present invention comprises sequentially impregnating the support with solutions or dispersions of each component compound, drying and calcining the impregnated support.

The calcining step will be accomplished under conditions which ensure the conversion of any nonoxide or nonphosphate compounds to the oxide or phosphate form and the volatilizing of any undesired elements. In general the calcining step comprises heating the catalyst composition to a temperature in the range of about 800° to about 1500° F for a time in the range of about 1 to 40 hours. Presently preferred calcining conditions comprise a temperature in the range of about 850° to about 1400° F for a time in the range of about 2 to about 24 hours in the presence of a molecular oxygen-containing gas, for example, air.

Suitable feeds for conversion to furan compounds include the unsaturated acyclic hydrocarbons, particularly the acyclic alkenes and acyclic alkadienes having from 4 to 10 carbon atoms. Examples include n-butene-1, butene-2, n-pentene-1, isopentene, hexene-1, heptene-2, octene-1, decene-1, 2-methylbutene-1, hexene-3, 2-ethylbutene-1, 2-methylpentene-3, 3-ethylhexene-2, butadiene-1,3, pentadiene-1,3, isoprene, hexadiene-1,3, decadiene-1,3, and the like, and mixtures thereof. The acyclic alkadienes having from 4 to 5 carbon atoms are presently preferred.

The furan compounds produced by the process of the present invention have the formula

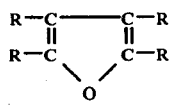

wherein each R is individually selected from the group consisting of hydrogen and alkyl radicals having from 1 to 6 carbon atoms, the total carbon atoms in the R radicals being in the range of 0 to 6. Representative products include furan, 2-methylfuran, 3-methylfuran, 2,5-diethylfuran, 2-n-hexylfuran, 2-isopropyl-3methylfuran, 3,4-di(n-propyl)furan, 3-methyl-4-n-butylfuran and the like.

In accordance with the present invention a hydrocarbon feed comprising one or more acyclic alkenes and/or one or more acyclic alkadienes is contacted, under suitable reaction conditions for conversion to furan compounds, with a molecular oxygen containing gas in the presence of the hereinabove defined catalyst. The molecular oxygen containing gas can be high purity oxygen, oxygen diluted with an inert diluent such as nitrogen, flue gas containing residual oxygen, air, or any other source of molecular oxygen which is at least essentially free of contaminants which would be detrimental to the desired reaction. In a presently preferred embodiment, the oxidative dehydrogenation process is carried out in the absence of any halogen. In general, the temperature will be in the range of about 500° to about 1200° F., and preferably will be in the range of about 700° to about 1100° F. Any suitable pressure can be employed, but in general the pressure will be in the range of about 0.05 to about 250 psig, and preferably will be in the range of about 0.1 to about 25 psig. The hydrocarbon feed rate will generally be in the range of about 10 to about 1000 standard cubic feet of alkenes and/or alkadienes per hour per cubic foot of catalyst bed (GHSV), and preferably will be in the range of about 100 to about 500 GHSV. The mol ratio of molecular oxygen to alkenes and alkadienes will generally be in the range of about 0.1:1 to about 3:1, and preferably will be in the range of about 0.5:1 to about 2:1. Steam can be employed in the reaction zone as a diluent and heat transfer agent. When steam is utilized, the mol ratio of steam to alkenes and alkadienes will generally be in the range of about 0.1:1 to about 50:1, and preferably will be in the range of about 5:1 to about 30:1.

The alkenes, if present, are largely converted to the corresponding alkadienes. The alkadienes, in turn, are converted in significant quantities to the corresponding furan compounds. However, the reaction effluent can also contain unreacted feed material, alkenes including ethylene, propylene and butenes, water, oxides of carbon, alkenylcycloolefin, 4-vinylcyclohexane, crotonaldehyde, acetaldehyde and other oxygenated products. The furan compounds can be recovered by suitable techniques, for example by condensation from the reactor gas effluent followed by distillation. Unconverted alkenes and/or alkadienes can be recovered and recycled to the reactor, as can other materials such as crotonaldehyde which are convertible to furan compounds under the reaction conditions. If desired, the conversion of alkenes to furan compounds can be conducted in two reaction zones in series. The first reaction zone can be operated under conditions favorable for the conversion of the alkenes to alkadienes, while the second reaction zone can be operated under conditions favorable to the conversion of the alkadienes to furan compounds. The effluent from the first reaction zone can be subjected to conventional separation techniques to recover unconverted alkenes for recycle to the first reaction zone and a concentrated alkadiene stream for feed to the second reaction zone. If desired, the total effluent from the first reaction zone can be passed directly to the second reaction zone without separation. The effluent of the second reaction zone can be processed for recovery and recycle of unreacted alkadienes to the second reaction zone and for recovery of a furan compound product. The catalyst of the present invention can be employed in both reaction zones, or another suitable dehydrogenation catalyst can be employed in the first reaction zone while the present catalyst is utilized in the second reaction zone.

The following example is presented in further illustration of the invention and should not be construed in undue limitation thereof.

EXAMPLE

In a series of runs, 400 GHSV butadiene, 400 GHSV oxygen and 8000 GHSV steam were contacted in the presence of about 2 cubic centimeters of the respective catalyst. Other reaction conditions and results are set forth in the following table:

TABLE

| Run | Atom Ratio Iron/P | Temperature ° F | Conversion of Butadiene % | Furan Yield Mole % | Selectivity to Furan % | Acetaldehyde Yield Mole % | Selectivity to Furan and Acetaldehyde % |
|---|---|---|---|---|---|---|---|
| 1 | 0.94/1 | 1000 | 16.3 | 12.5 | 76.7 | 0.4 | 78.9 |
| 2 | 0.87/1 | 1000 | 4.8 | 1.4 | 28.9 | 0 | 28.9 |
| 3 | 0.87/1 | 1000 | 2.5 | 0.1 | 4.0 | 0 | 4.0 |
| 4 | 3.13/1 | 800 | 5.4 | 2.1 | 38.8 | 0 | 38.8 |
| 5 | " | 900 | 24.0 | 7.0 | 29.2 | 0.5 | 31.3 |
| 6 | " | 1000 | 26.9 | 5.7 | 21.1 | 0.3 | 22.4 |
| 7 | 5.41/1 | 900 | 26.6 | 7.7 | 28.9 | 0.6 | 31.1 |
| 8 | " | 1000 | 25.3 | 6.4 | 25.3 | 0.2 | 26.0 |
| 9 | 4.35/1 | 900 | 7.6 | 3.3 | 43.8 | 0 | 43.8 |
| 10 | " | 1000 | 22.9 | 6.6 | 28.8 | 0.2 | 29.8 |
| 11 | 1.45/1 | 1000 | 4.7 | 0.2 | 4.3 | 0 | 4.3 |
| 12 | 3.13/1 | 900 | 12.2 | 2.0 | 16.4 | 0 | 16.4 |
| 13 | " | 1000 | 25.4 | 5.4 | 21.2 | 0.2 | 22.0 |
| 14 | 5.41/1 | 900 | 26.6 | 4.5 | 16.8 | 0 | 16.8 |
| 15 | " | 1000 | 29.0 | 5.7 | 19.8 | 0 | 19.8 |
| 16 | 1/1 | 900 | 1.0 | 0 | 0 | 0 | 0 |
| 17 | 0.72/1 | 1000 | 1.3 | 0 | 0 | 0 | 0 |
| 18 | 0.72/1 | 1100 | 7.4 | 1.8 | 24.0 | 0 | 24.0 |
| 19 | 0.62/1 | 1000 | 1.0 | 0 | 0 | 0 | 0 |
| 20 | 0.62/1 | 1100 | 6.9 | 2.5 | 35.9 | 0 | 35.9 |

TABLE-continued

| Run | Atom Ratio Iron/P | Temperature °F | Conversion of Butadiene % | Furan Yield Mole % | Selectivity to Furan % | Acetaldehyde Yield Mole % | Selectivity to Furan and Acetaldehyde % |
|---|---|---|---|---|---|---|---|
| 21 | 0.54/1 | 1000 | 1.0 | 0 | 0 | 0 | 0 |
| 22 | 0.51/1 | 1100 | — | — | — | — | — |

Runs for the catalysts of runs 1 to 15 were generally made with each catalyst at 700°, 800°, 900°, and 1000° F, and only those runs producing significant quantities of furan are shown. The runs for the catalysts of runs 17 to 22 were made only at the indicated temperature. The catalysts of runs 1-2, 4-10 were prepared by mixing together sufficient $Fe_2O_3$ and $H_3PO_4$ to give the atom ratios shown in the Table. The quantity of catalyst prepared was about 20 grams or less. Each mixture was calcined at 850° F for 7 hours, then at 1000° F for 11 hours. The catalysts of runs 3 and 11-15 were prepared by mixing together sufficient $Fe_2O_3$ and $NH_4H_2PO_4$ to give the atom ratios shown in the Table. The catalyst of run 16 was made by pouring sufficient $H_3PO_4$ over $Fe_2O_3$ to give the atom ratio shown in the Table. After soaking, without stirring, the mixture was calcined at 1000° F for 17 hours. This mixture was prepared to give an inhomogeneous catalyst.

The catalysts of runs 17-22 were prepared by mixing together sufficient $Fe_2O_3$ and $H_3PO_4$ to give the atom ratios shown in the Table. Each mixture was calcined at 1000° F for 18 hours. About 20 gram lots of catalyst were prepared. Each mixture was calcined at 1200° F for 24 hours.

The gaseous effluents, on a dry basis, were analyzed by means of gas-liquid chromatography. Products found included unreacted butadiene, furan, acetaldehyde, carbon oxides, ethylene, propylene and butenes. The reported selectivities to furan and furan plus acetaldehyde are modified selectivities based on the above gaseous product analyses. The yields of furan and acetaldehyde are in terms of mols per 100 mols of butadiene feedstock.

Runs 1-3 are made with prior art catalysts, rich in phosphorus. The results show that a catalyst with a Fe/P ratio of 0.94/1 is effective in producing substantial amounts of furan from a relatively modest conversion (16.3%) of butadiene. The catalyst of run 1 was non-uniform in appearance with mixed red and white portions. It is believed the active portions of the catalyst reside in the interfaces between the red and white portions and hence the true iron/phosphorus ratio is unknown. The catalyst of run 16 was made in an effort to obtain a similar non-homogeneous catalyst composition. The results showed the latter catalyst to be inactive at the conditions used. Thus the catalyst of run 1 may be a fluke. However, the results also indicate that a catalyst even slightly richer in phosphorus is much less effective in converting butadiene (4.8 and 2.5% in separate runs) to furan (1.4% and 0.1%).

The catalysts of the invention are phosphorus-poor. That is, the iron/phosphorus ratio is at least 2/1 rather than being less than 1/1 as in prior art catalysts. Inspection of the data indicate that significant quantities of furan are produced when the Fe/P ratio ranges from about 3/1 to about 6/1. The data show a minimum amount of furan is produced at a Fe/P ratio of about 1.45/1 to some value approaching 0.94/1. Thus an unexpected criticality in operably ranges of phosphorus-poor Fe/P catalysts is shown by the data.

Reasonable variations and modifications are possible within the scope of the foregoing disclosure and the appended claims to the invention.

We claim:
1. A composition consisting essentially of phosphorus, iron and oxygen, with the iron-to-phosphorus atom ratio being in the range of 2:1 to about 20:1.
2. A composition in accordance with claim 1 wherein said ratio is in the range of about 2.5:1 to about 10:1.
3. A composition in accordance with claim 1 wherein said ratio is in the range of about 3:1 to about 6:1.
4. An oxidative dehydrogenation catalyst composition in accordance with claim 1 further consisting essentially of solid catalyst support constituting from about 10 to about 98 weight percent of the total catalyst composition.
5. A composition in accordance with claim 4 wherein said solid catalyst support is selected from the group consisting of zinc oxide, silica, alumina, boria, magnesia, titania, zirconia, and mixtures thereof.
6. A composition in accordance with claim 5 wherein said solid catalyst support constitutes from about 75 to about 95 weight percent of the total catalyst composition.
7. A composition in accordance with claim 4 wherein said solid catalyst support has a surface area in the range of about 2 to about 50 m²/g.
8. A composition in accordance with claim 4 wherein said solid catalyst support has a surface area in the range of about 5 to about 20 m²/g.
9. A composition in accordance with claim 4 wherein said ratio is in the range of about 2.5:1 to about 10:1.
10. A composition in accordance with claim 4 wherein said ratio is in the range of about 3:1 to about 6:1.
11. A composition in accordance with claim 1 wherein the composition is a calcined mixture of $Fe_2O_3$ and $H_3PO_4$.
12. A composition in accordance with claim 1 wherein the composition is a calcined mixture of $NH_4H_2PO_4$ and $Fe_2O_3$.
13. A composition consisting of phosphorus, iron and oxygen, with the iron-to-phosphorus atom ratio being in the range of 2:1 to about 20:1.
14. A composition in accordance with claim 13 wherein said ratio is in the range of about 2.5:1 to about 10:1.
15. A composition in accordance with claim 13 wherein said ratio is in the range of about 3:1 to about 6:1.
16. A composition in accordance with claim 13 wherein the composition is a calcined mixture of $Fe_2O_3$ and $H_3PO_4$.
17. A composition in accordance with claim 13 wherein the composition is a calcined mixture of $NH_4H_2PO_4$ and $Fe_2O_3$.

* * * * *